United States Patent
Price

(10) Patent No.: US 10,306,886 B2
(45) Date of Patent: *Jun. 4, 2019

(54) LACTAM SOLUBILITY

(71) Applicant: Conopco, Inc., Englewood Cliffs, NJ (US)

(72) Inventor: Paul Damien Price, Wirral (GB)

(73) Assignee: CONOPCO INC., Englewood Cliffs, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/750,910

(22) PCT Filed: Aug. 4, 2016

(86) PCT No.: PCT/EP2016/068625
§ 371 (c)(1),
(2) Date: Feb. 7, 2018

(87) PCT Pub. No.: WO2017/029118
PCT Pub. Date: Feb. 23, 2017

(65) Prior Publication Data
US 2018/0228153 A1 Aug. 16, 2018

(30) Foreign Application Priority Data
Aug. 20, 2015 (EP) .................... 15181847

(51) Int. Cl.
*A01N 43/36* (2006.01)
*A61K 8/49* (2006.01)
*A61Q 17/00* (2006.01)
*A01N 25/02* (2006.01)
*A61K 8/34* (2006.01)
*A61Q 15/00* (2006.01)

(52) U.S. Cl.
CPC .............. *A01N 43/36* (2013.01); *A01N 25/02* (2013.01); *A61K 8/34* (2013.01); *A61K 8/4913* (2013.01); *A61Q 15/00* (2013.01); *A61Q 17/005* (2013.01); *A61K 2800/49* (2013.01)

(58) Field of Classification Search
CPC ........................................ A01N 43/36
See application file for complete search history.

(56) References Cited

U.S. PATENT DOCUMENTS

| 5,955,419 | A  | 9/1999  | Barket, Jr. et al. |
| 8,641,948 | B2 | 2/2014  | Ghogh et al. |
| 9,586,901 | B2 | 3/2017  | Kumar et al. |
| 9,930,888 | B2 | 4/2018  | Parry et al. |
| 2011/0059144 | A1 | 3/2011 | Fletcher et al. |
| 2014/0294925 | A1 | 10/2014 | Yin |
| 2015/0351393 | A1 | 12/2015 | Parry et al. |

FOREIGN PATENT DOCUMENTS

| WO | WO2006085089 | 8/2006 | |
| WO | WO2007085042 | 8/2007 | |
| WO | WO-2007085042 A1 * | 8/2007 | .......... C07D 207/36 |
| WO | WO2010069742 | 6/2010 | |
| WO | WO-2010069742 A1 * | 6/2010 | .......... C11D 3/2096 |
| WO | WO2014118240 | 8/2014 | |
| WO | WO-2014118240 A1 * | 8/2014 | ............. A01N 43/36 |

OTHER PUBLICATIONS

Wei et al., Measurement and Correlation of the Solubility of Penicillin V Potassium in Ethanol + Water and 1-Butyl Alcohol + Water Systems, J. Chem. Eng. Data, 2015, 60 (1), pp. 112-117, DOI: 10.1021/je5008422, Publication Date (Web): Dec. 15, 2014.*
U.S. Appl. No. 15/750,890, filed Feb. 2018, O'Keefe.*
Carla S.M. Pereira et al., Ethyl lactate as a solvent: properties, applications and production processes—a review, Green Chemistry, 2011, pp. 2658-2671; XP055235519, vol. 13, No. 10.
IPRP in PCTEP2016069072, dated Aug. 2, 2017.
IPRP2 in PCTEP2016068585, dated Nov. 2, 2017.
IPRP2 in PCTEP2016068625, dated Sep. 6, 2017.
Mary E. Davey et al., Rhamnolipid Surfactant production Affects Biofilm Architecture in Pseudomonas aeruginosa PAO1, Journal of Bacteriology, 2003, pp. 1027-1036, vol. 185, No. 3, American Society for Microbiology.
Ondrej Krenk et al., Methodology for Synthesis of Enantiopure 3,5-Disubstituted Pyrrol-2-ones, European Journal of Organic Chemistry, 2015, pp. 5414-5423; XP002752111.
Search Report & Written Opinion in EP15181849, dated Feb. 23, 2016.
Search Report & Written Opinion in PCTEP2016069072, dated Sep. 14, 2016.
Search Report and Written Opinion in PCTEP2016067613, dated Sep. 21, 2016.
Search Report and Written Opinion in PCTEP2016067616, dated Sep. 12, 2016.
Search Report and Written Opinion in PCTEP2016068008, dated Sep. 12, 2016.
Search Report and Written Opinion in PCTEP2016068010, dated Sep. 12, 2016.
Search Report and Written Opinion in PCTEP2016068287, dated Oct. 26, 2016.
Search Report and Written Opinion in PCTEP2016068585, dated Oct. 4, 2016.
Search Report and Written Opinion in PCTEP2016068625, dated Sep. 9, 2016.
Search Report in EP15181842, dated Dec. 10, 2015.
Search Report in EP15181846, dated Dec. 11, 2015.
Search Report in EP15181847, dated Dec. 17, 2015.
Search Report in EP15181851, dated Dec. 11, 2015.

(Continued)

*Primary Examiner* — Svetlana M Ivanova
(74) *Attorney, Agent, or Firm* — Foley & Lardner LLP

(57) ABSTRACT

Compositions comprising a lactam and an alcohol. The compositions are suitable for use as anti-microbial, anti-biofilm and bacteriostatic compositions.

9 Claims, No Drawings

(56) References Cited

OTHER PUBLICATIONS

Search Report in EP15181856, dated Dec. 14, 2015.
Search Report in EP15181858, dated Dec. 11, 2015.
Written Opinin in EP15181856, dated Dec. 14, 2015.
Written Opinion 2 in PCTEP2016067613, dated Jul. 11, 2017.
Written Opinion in EP15181842, dated Dec. 10, 2015.
Written Opinion in EP15181846, dated Dec. 11, 2015.
Written Opinion in EP15181847, dated Dec. 17, 2015.
Written Opinion in EP15181851, dated Dec. 11, 2015.
Written Opinion in EP15181858, dated Dec. 11, 2015.
Wei et al.; Measurement and Correlation of the Solubility of Penicillin V Potassium in Ethanol + Water and 1-Butyl Alcohol + Water Systems; Journal of Chemical and Engineering Data; 2015; 112-117; vol. 60, No. 1.

* cited by examiner

LACTAM SOLUBILITY

This application claims priority from EP 15181847.3 filed 20 Aug. 2015 which is herein incorporated by reference for all purposes.

The present invention relates to compositions comprising lactams and an alcohol. The compositions are suitable for use as anti-microbial, anti-biofilm and bacteriostatic compositions.

WO 2007/085042 and WO 2004/016588 disclose lactams for antimicrobial benefit and steps towards their synthesis. WO2014/118240 discloses antimicrobial compositions comprising a lactam and a hydrotope.

However, use of these lactams is limited by relatively low solubility, especially in aqueous compositions.

The present invention relates to combinations of lactams and an alcohol. The combination has been shown to improve lactam solubility.

More specifically, the present invention relates to lactams as described in WO 2007/085042 and WO 2004/016588 in combination with an alcohol. The contents of WO 2007/085042 and WO 2004/016588, and in particular the lactam structures explicitly drawn out therein, are incorporated by reference.

For example, in a first aspect, the present invention relates to a composition comprising a lactam and an alcohol, wherein the lactam is a lactam of formula (I) or (II):

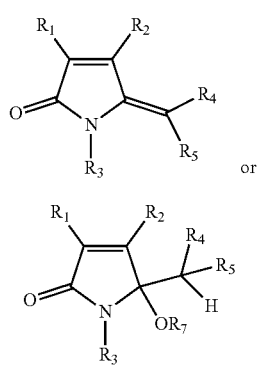

wherein:

$R_1$ and $R_2$ are each independently selected from hydrogen, halogen, alkyl, cycloalkyl, alkoxy, oxoalkyl, alkenyl, heterocyclyl, heteroaryl, aryl and aralalkyl; and $R_3$ is selected from hydrogen, hydroxyl, alkyl, cycloalkyl, alkoxy, oxoalkyl, alkenyl, heterocyclyl, heteroaryl, cycloalkyl, aryl, aralalkyl and —C(O)CR$_6$=CH2;

$R_4$ and $R_5$ are independently selected from hydrogen, aryl, heterocyclyl, heteroaryl, and arylalkyl; and $R_6$ is selected from hydrogen and methyl; and $R_7$ is selected from hydrogen and —C(O)CR$_6$=CH$_2$; and Preferably, at least one of $R_4$ and $R_5$ is hydrogen.

It will be appreciated that, where appropriate groups may be optionally substituted. Optional substituents may include halogens, $C_{1-4}$alkyl, $C_{1-4}$haloalkyl (for example, $CF_3$) and $C_{1-4}$alkoxy.

Alkyls may, for example, be $C_{1-12}$alkyls, such as $C_{1-6}$ alkyls. Aryls may, for example, be $C_{6-10}$aryls, for example, phenyls.

Preferably, at least one of $R_1$ and $R_2$ is selected from heterocyclyl, heteroaryl, aryl and arylalkyl.

Preferably, $R_1$ is hydrogen. Preferably, $R_3$ is hydrogen. Preferably, $R_4$ is hydrogen. Preferably, $R_5$ is hydrogen. Preferably, $R_6$ is hydrogen. Preferably, $R_7$ is hydrogen. Preferably, $R_2$ is aryl or aralalkyl. More preferably, $R_2$ is a phenyl group or a substituted phenyl group, for example, a mono-substituted phenyl group. Substitution may be ortho, meta, or para. Preferably, it is para. Preferred substituents include halogen and methyl. For example, and without limitation, $R_2$ may be selected from phenyl, 4-fluorophenyl, 4-chlorophenyl, 4-bromophenyl and 4-methylphenyl.

Accordingly, in a first aspect, the present invention may provide to a composition comprising a lactam and an alcohol, wherein the lactam is a lactam of Formula Ia or Formula IIa:

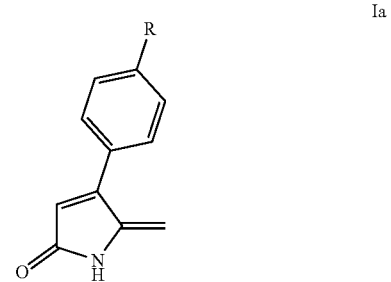

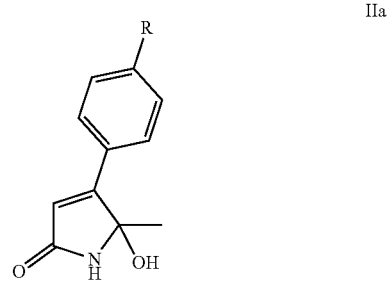

wherein R is H, halogen (preferably, F, Cl, or Br), or $C_{1-4}$alkyl (preferably methyl).

In some embodiments, the lactam is a lactam of formula Ia. In some embodiments, the lactam is a lactam of formula IIa.

Preferred lactams may include:

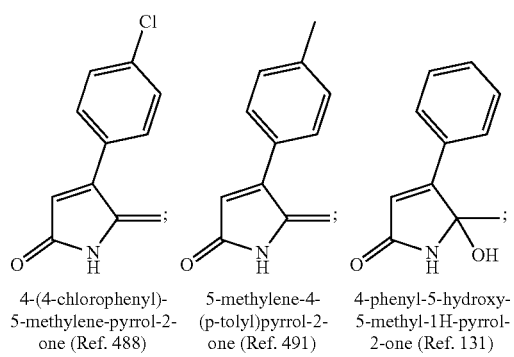

4-(4-chlorophenyl)-5-methylene-pyrrol-2-one (Ref. 488)

5-methylene-4-(p-tolyl)pyrrol-2-one (Ref. 491)

4-phenyl-5-hydroxy-5-methyl-1H-pyrrol-2-one (Ref. 131)

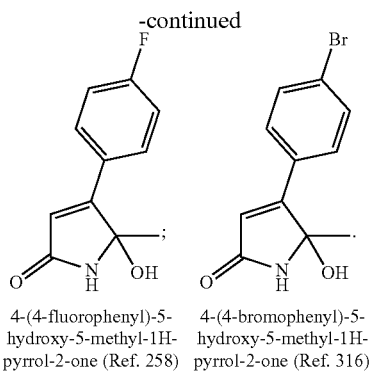

4-(4-fluorophenyl)-5-hydroxy-5-methyl-1H-pyrrol-2-one (Ref. 258)

4-(4-bromophenyl)-5-hydroxy-5-methyl-1H-pyrrol-2-one (Ref. 316)

The composition may be aqueous or non-aqueous. Preferably, the composition miscible with water. For example, the composition may be alcohol-based or alcohol-water-based.

The composition may be, without limitation, any of a personal care composition, a homecare composition, a pharmaceutical composition, or an industrial composition such as an anti-biofilm coating or paint, for example, for use in maritime environments. The composition may also be an agricultural chemical. The compositions may be suitable for use as antimicrobial, anti-biofilm and bacteriostatic compositions. Non-limiting examples of such compositions are provided herein. The compositions may also be used as additive compositions; in other words, the composition may be combined with further ingredients such as excipients to form a composition as described above.

Preferably, the composition has a high alcohol content (for example at least 50% wt. of the composition). Such compositions may be useful as, for example, deodorant compositions.

Suitably, the alcohol is a $C_{1-6}$ alkyl alcohol. It may be a mono-alcohol or a polyol. For example, in some cases, the alcohol is a $C_{1-6}$ alkyl alcohol having 1, 2, or 3 OH groups. For example, the alcohol may comprise one, two, or three carbon atoms.

The alkyl may, where appropriate, be straight chain or branched. The or each OH group may be primary, secondary or tertiary.

In some cases, the alcohol is a mono-alcohol having one to three carbon atoms.

Certain preferred alcohols include methanol, ethanol, propanol, and glycerol. Methanol and ethanol are preferred, with ethanol being most preferred.

The composition may comprise at least 10% wt. alcohol, for example, at least 15% wt. alcohol, or higher amounts such as 20% wt., 25% wt., 30% wt, 40% wt, or even as high as 50% wt. In some cases, the composition comprises even high amounts of alcohol, for example at least 60% wt., at least 70% wt., alcohol.

For example, the may comprise 10-50% wt. of alcohol, such as 10-25% wt. or higher amounts such as 25-50% wt. It will be apparent that the amount of alcohol may be selected to suit the intended use of the composition. For example, higher amounts of alcohol may permit larger lactam loadings, but may be less preferred for personal care compositions. It will be appreciated that higher amounts may be especially useful for industrial and agricultural compositions such as paints.

Preferably the composition contains 0.000001 to 50% wt. lactam, more preferably 0.001 to 50% wt. even more preferably 0.01 to 5% wt., most preferably 0.01 to 2%.

DESCRIPTION

Lactams may be obtained using methods as described in WO 2007/085042 and WO 2004/016588, which are herein incorporated by reference in their entirety.

Compositions

The compositions described herein may be compositions having anti-microbial activity. In some cases, the compositions are anti-bacterial. They may have bactericidal and/or bacteriostatic activity. The inventor(s) have observed desirable bacteriostatic activity. Accordingly, in some cases, the composition is a bacteriostatic composition.

The compositions may also prevent and/or inhibit biofilm formation. Biofilms are formed when microorganisms stick to a surface. Biofilm extracellular polymeric substances may be formed. Biofilms (also referred to as slime) present problems in industrial environments; for example, they may form in pipes in apparatus, or industrial and agricultural structures, on solar panels, and on boat hulls and other marine structures. Biofilms may also pose a problem in domestic environments. For example, biofilms may form in domestic appliances such as washing machines. Biofilms are also present in personal care, for example, they may form on tooth surfaces.

Compositions suitable for any and all of these applications are within the scope of the invention. In some cases, the composition is a paint or other coating. In such cases, the composition may further comprise a binder, optionally a pigment and optionally one or more conventional additives (for example, to modify surface tension, improve flow properties, improve the finished appearance, increase wet edge, improve pigment stability, etc—such additives are known in the art). The composition may comprise an aqueous solvent or an organic solvent to suit purpose.

The composition may also be used in medical applications, for example to coat equipment including medical devices.

In some cases, the composition is a pharmaceutical composition. In other words, the composition may comprise a lactam as described herein and a pharmaceutically acceptable excipient. The composition may be suitable for topical use (for example, it may be a cream or lotion), it may be suitable for ocular use (for example, it may be an used as a pharmaceutical eye drop), it may be suitable for otic use (for example, it may be used as an ear drop), it may be suitable as a mouth wash, or it may be suitable for oral administration.

In some cases, the composition is a composition suitable for use in the home (often referred to as a homecare composition) or institutions. Homecare compositions include, without limitation, cleaning products, laundry detergents, and fabric conditioners. In some cases, the composition is a homecare composition, for example a laundry liquid. The composition may therefore comprise a detergent surfactant and a builder. The composition may be a fabric conditioner (also called a fabric softener) and may comprise an antistatic agent. The composition may also be a domestic cleaning product.

In some cases, the composition is a personal care composition. For example, the composition may be intended for use on the skin (for example, a cream, cleanser or serum). For example, the composition may be useful in the prevention or treatment of acne. For example, the composition may comprise one or more of dimethicone, petrolatum, a humectant such as hyaluronic acid or glycerin; and ceramide(s). In some cases, the composition is a personal care composition comprising a detergent, for example, the composition may be a face wash or shower gel or hair shampoo. The composition may be a hair treatment composition other than a shampoo. The composition may be a deodorant composition (for example, a deodorant powder, paste or liquid). The composition may be an oral care composition (such as a toothpaste or mouthwash and may include, for example, fluoride and/or flavourings.

In some cases, the composition is a contact lens cleaning fluid.

The composition may be a composition suitable for use in agriculture, for example, as a soil additive (solid or liquid).

The composition may be a composition suitable for use in the treatment of or manufacture of glass or lens for example as an additive/treatment for solar panels.

EXAMPLES

The following example uses, without limitation, 4-(4-chlorophenyl)-5-methylene-pyrrol-2-one.

Excess solid lactam (~3 mg) was placed in a Whatman® Mini Uniprep sample vial, fitted with a 0.45 µm nylon filter. Water or water+alcohol (500 µL) was added the mixture shaken and tapped briefly to initially disperse the solid and the mixture then agitated for 48 hours using a plate shaker fitted with a vial holder (see image below). After 48 hours, the solid was removed from the system by pressing down the plunger with integral filter on the vial (see image below). This removes the solid and provides filtered solution within the inner chamber which is then ready for analysis.

The level of lactam dissolved in solution was quantified using HPLC analysis. Samples were analysed on an Agilent 1200® series HPLC fitted with a Thermo Hypersil® Gold C18 column (15×2.1×3 µm), isocratic elution with 60/40 methanol/water (+0.1% Formic Acid), 0.4 mL/min flow rate, using a DAD detector at 285 nm. 4-(4-chlorophenyl)-5-methylene-pyrrol-2-one has a retention time of ~2.8 minutes.

The absolute level of lactam in solution is measured and reported as an increase in solubility of lactam relative to water alone. The results are shown below.

| Additive | % Additive in Water | Mean Lactam Level in Solution (ppm) | Solubility Increase vs water alone |
|---|---|---|---|
| MeOH | 0 | 6.2 | 1.00 |
|  | 0.5 | 7.5 | 1.20 |
|  | 1 | 9.0 | 1.45 |
|  | 2 | 8.2 | 1.32 |
|  | 5 | 10.4 | 1.67 |
|  | 10 | 15.7 | 2.52 |
|  | 25 | 48.8 | 7.87 |
|  | 50 | 315.6 | 50.90 |
| EtOH | 0 | 6.2 | 1.00 |
|  | 0.5 | 7.9 | 1.27 |
|  | 1 | 8.9 | 1.44 |
|  | 2 | 10.7 | 1.73 |
|  | 5 | 13.4 | 2.16 |
|  | 10 | 18.3 | 2.95 |
|  | 25 | 82.1 | 13.24 |
|  | 50 | 1800.2 | 290.35 |
| Glycerol | 0 | 5.7 | 1.00 |
|  | 0.5 | 1.7 | 0.29 |
|  | 1 | 2.3 | 0.41 |
|  | 2 | 3.1 | 0.54 |
|  | 5 | 5.2 | 0.91 |
|  | 10 | 9.0 | 1.59 |
|  | 25 | 15.8 | 2.77 |
|  | 50 | 95.3 | 16.72 |

It will be appreciated that, except where expressly provided otherwise, all preferences are combinable.

The invention claimed is:

1. A composition comprising a lactam and an alcohol, wherein the lactam is a lactam of Formula Ia or Formula IIa:

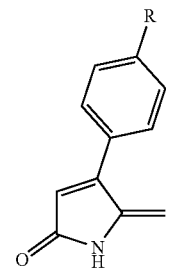

Ia

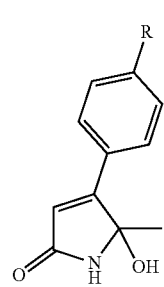

IIa wherein R is H, halogen, or $C_{1-4}$alkyl; and wherein the composition has at least 30% wt. alcohol content.

2. The composition of claim 1, wherein R is H, F, Cl, Br, or Me.

3. The composition of claim 1, wherein the lactam is selected from:

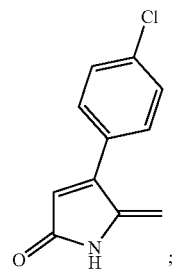

(Ref. 488)

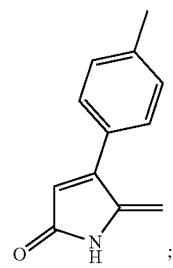

(Ref. 491)

(Ref. 131)

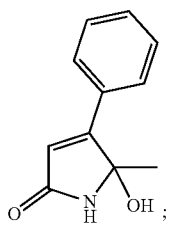

(Ref. 258)

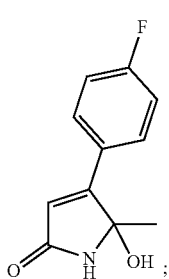

(Ref. 316)

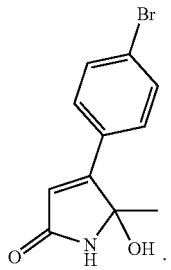

4. The composition of claim 1, wherein the alcohol is a $C_{1-6}$ alkyl alcohol.

5. The composition of claim 1, wherein the alcohol is selected from methanol, ethanol, propanol, and glycerol, optionally wherein the alcohol is methanol or ethanol.

6. The composition of claim 1, wherein the alcohol is a mono-alcohol.

7. The composition of claim 1, wherein the alcohol is ethanol.

8. The composition of claim 1, wherein the composition has at least 50% wt. alcohol content.

9. The composition of claim 1, wherein the composition is a personal care deodorant composition.

* * * * *